United States Patent
Cvetovich et al.

(10) Patent No.: US 6,814,895 B2
(45) Date of Patent: Nov. 9, 2004

(54) PROCESS FOR THE SYNTHESIS OF 1-(3,5-BIS(TRIFLUOROMETHYL)PHENYL)ETHAN-1-ONE

(75) Inventors: Raymond Cvetovich, Scotch Plains, NJ (US); Tomoyuki Asai, Kanagawa-ku (JP); Yoshiko Yodogawa, Nishinomiya (JP)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/451,293

(22) PCT Filed: Dec. 18, 2001

(86) PCT No.: PCT/US01/48800
§ 371 (c)(1),
(2), (4) Date: Jan. 28, 2004

(87) PCT Pub. No.: WO02/50009

PCT Pub. Date: Jun. 27, 2002

(65) Prior Publication Data

US 2004/0108603 A1 Jun. 10, 2004

Related U.S. Application Data

(60) Provisional application No. 60/256,790, filed on Dec. 20, 2000.

(51) Int. Cl.$^7$ .............................. C07F 3/00; C07C 45/00
(52) U.S. Cl. .................................... 260/665 G; 568/319
(58) Field of Search ..................... 260/665 G; 568/319, 568/335

(56) References Cited

U.S. PATENT DOCUMENTS

| | | |
|---|---|---|
| 4,450,296 A | 5/1984 | Yoshida |
| 5,142,092 A | 8/1992 | Kysela et al. |
| 5,235,068 A | 8/1993 | Minai et al. |
| 5,510,507 A | 4/1996 | Ayers et al. |
| 6,129,863 A * | 10/2000 | Lee et al. ............... 260/665 G |
| 6,235,222 B1 * | 5/2001 | Mitsui et al. ........... 260/665 G |
| 6,248,265 B1 | 6/2001 | Lee et al. |
| 6,255,545 B1 | 7/2001 | Cvetovich et al. |
| 6,350,915 B1 | 2/2002 | Cvetovich et al. |

FOREIGN PATENT DOCUMENTS

| | | |
|---|---|---|
| WO | WO 00/76947 | 12/2000 |
| WO | WO 00/76948 | 12/2000 |
| WO | WO 01/02326 | 1/2001 |

OTHER PUBLICATIONS

March J. *"Advanced Organic Chemistry: Reactions, Mechanisms, and Structure"* McGraw–Hill Book Company, (New York), 1968, pp. 475–476, entire document.

Leazer, J.L., *J. Org. Chem.*, 2003, 68, 3695–3698 (Apr. 19, 2003).

* cited by examiner

*Primary Examiner*—Jean F. Vollano
(74) *Attorney, Agent, or Firm*—J. Eric Thies; Melvin Winokur

(57) ABSTRACT

The present invention is concerned with a novel process for the preparation of 1-(3,5-bis(trifluoromethyl)phenyl)ethan-1-one (CAS 30071-93-3). This compound is useful as an intermediate in the synthesis of therapeutic agents.

20 Claims, No Drawings

PROCESS FOR THE SYNTHESIS OF 1-(3,5-BIS(TRIFLUOROMETHYL)PHENYL)ETHAN-1-ONE

CROSS REFERENCE TO RELATED APPLICATIONS

This application is a U.S. National Phase application under 35 U.S.C. § 371 of PCT Application No. PCT/US01/48800, filed Dec. 18, 2001, which claims priority under 35 U.S.C. § 119 (e) from Provisional Application No. 60/256,790, Filed Dec. 20, 2000.

BACKGROUND OF THE INVENTION

The present invention relates to processes for the preparation of 1-(3,5-bis(trifluoromethyl)phenyl)ethan-1-one (CAS 30071-93-3) which is useful as an intermediate in the preparation of therapeutic agents. In particular, the present invention provides a process for the preparation of 1-(3,5-bis(trifluoromethyl)-phenyl)ethan-1-one which is an intermediate in the synthesis of pharmaceutical compounds which are substance P (neurokinin-1) receptor antagonists.

The general processes disclosed in the art for the preparation of 1-(3,5-bis(trifluoromethyl)phenyl)ethan-1-one result in relatively low and inconsistent yields of the desired product. In contrast to the previously known processes, the present invention provides effective methodology for the preparation of 1-(3,5-bis(trifluoromethyl)phenyl)ethan-1-one in relatively high yield and with a lower degree of exothermicity and, hence, a greater degree of safety.

It will be appreciated that 1-(3,5-bis(trifluoromethyl)phenyl)ethan-1-one is an important intermediate for a particularly useful class of therapeutic agents. As such, there is a need for the development of a process for the preparation of 1-(3,5-bis(trifluoromethyl)phenyl)ethan-1-one which is readily amenable to scale-up, uses cost-effective and readily available reagents and which is therefore capable of practical application to large scale manufacture.

Accordingly, the subject invention provides a process for the preparation of 1-(3,5-bis(trifluoromethyl)phenyl)ethan-1-one via a very simple, short and highly efficient synthesis.

SUMMARY OF THE INVENTION

The novel process of this invention involves the synthesis of 1-(3,5-bis(trifluoromethyl)phenyl)ethan-1-one. In particular, the present invention is concerned with novel processes for the preparation of a compound of the formula:

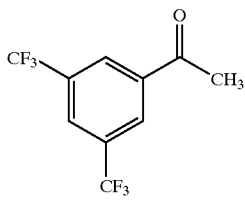

This compound is an intermediate in the synthesis of compounds which possess pharmacological activity. In particular, such compounds are substance P (neurokinin-1) receptor antagonists which are useful e.g., in the treatment of inflammatory diseases, psychiatric disorders, and emesis.

DETAILED DESCRIPTION OF THE INVENTION

The present invention is directed to processes for the preparation of 1-(3,5-bis(trifluoromethyl)phenyl)ethan-1-one of the formula:

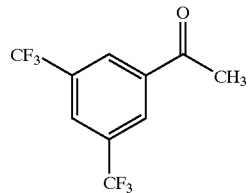

An embodiment of the general process for the preparation of 3,5-bis(trifluoromethyl)-benzoic acid is as follows:

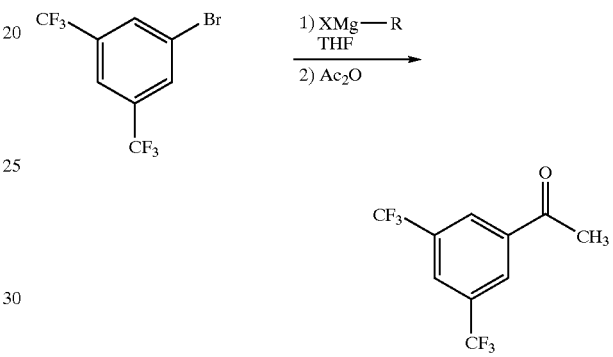

wherein:

X is selected from chloro, bromo and iodo; and

R is $C_{1-8}$alkyl.

In accordance with the present invention, the treatment of acetic anhydride with the Grignard reagent prepared by an exchange reaction between 3,5-bis(trifluoromethyl)bromobenzene and a $C_{1-8}$ alkyl magnesium halide provides 1-(3,5-bis(trifluoromethyl)phenyl)ethan-1-one in higher yields and in a safer, more efficient route than the processes disclosed in the art.

In the present invention, $C_{1-8}$ as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. In the present invention halo or halide is intended to include chloro, bromo and iodo.

In a preferred embodiment, the present invention is directed to a process for the preparation of 1-(3,5-bis(trifluoromethyl)phenyl)ethan-1-one which comprises the exchange reaction of 3,5-bis(trifluoromethyl)bromobenzene with a $C_{1-8}$alkyl magnesium halide in THF to form a Grignard reagent followed by addition of the Grignard reagent to acetic anhydride to give 1-(3,5-bis(trifluoromethyl)phenyl)-ethan-1-one.

Another embodiment of the present invention is directed to a process for the preparation of 1-(3,5-bis(trifluoromethyl)-phenyl)ethan-1-one which comprises the reaction of 3,5-bis(trifluoromethyl)bromobenzene with ethyl magnesium bromide in tetrahydrofuran to form 1-(3,5-bis(trifluoromethyl)phenyl)magnesium bromide followed by addition of the Grignard reagent to an excess of acetic anhydride to give 1-(3,5-bis(trifluoromethyl)phenyl)ethan-1-one.

A specific embodiment of the present invention concerns a process for the preparation of 1-(3,5-bis(trifluoromethyl) phenyl)magnesium bromide of the formula:

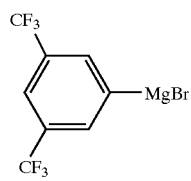

which comprises:

treating 3,5-bis(trifluoromethyl)bromobenzene of the formula:

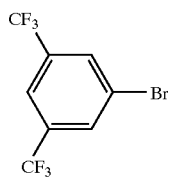

with a Grignard reagent selected from:

ethyl magnesium bromide, isopropyl magnesium chloride, ethyl magnesium chloride and isopropyl magnesium bromide, in an organic solvent to form 1-(3,5-bis(trifluoromethyl)phenyl)magnesium bromide.

Another specific embodiment of the present invention concerns a process for the preparation of 1-(3,5-bis(trifluoromethyl)phenyl)magnesium bromide of the formula:

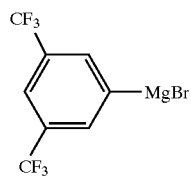

which comprises:

treating 3,5-bis(trifluoromethyl)bromobenzene of the formula:

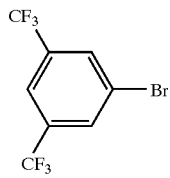

with ethyl magnesium bromide or isopropyl magnesium chloride in an organic solvent to form 1-(3,5-bis(trifluoromethyl)phenyl)magnesium bromide.

Another specific embodiment of the present invention concerns a process for the preparation of 1-(3,5-bis(trifluoromethyl)phenyl)ethan-1-one of the formula:

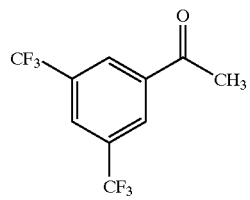

which comprises:

a) treating 3,5-bis(trifluoromethyl)benzene of the formula:

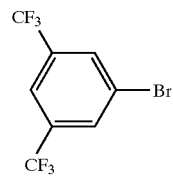

with a Grignard reagent selected from:

ethyl magnesium bromide, isopropyl magnesium chloride, ethyl magnesium chloride and isopropyl magnesium bromide, in an organic solvent to form a Grignard reagent of the formula:

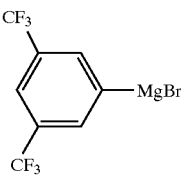

b) followed by contacting the Grignard reagent with acetic anhydride in an organic solvent to give 1-(3,5-bis(trifluoromethyl)phenyl)ethan-1-one of the formula:

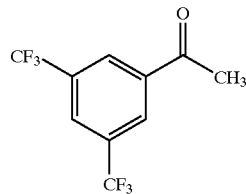

Another specific embodiment of the present invention concerns a process for the preparation of 1-(3,5-bis(trifluoromethyl)phenyl)ethan-1-one of the formula:

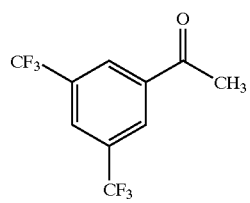

which comprises:

a) treating 3,5-bis(trifluoromethyl)benzene of the formula:

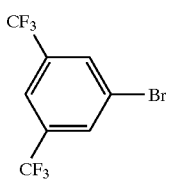

with a Grignard reagent selected from: ethyl magnesium bromide and isopropyl magnesium chloride, in an organic solvent to form a Grignard reagent of the formula:

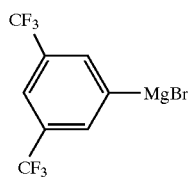

b) followed by contacting the Grignard reagent with acetic anhydride in an organic solvent to give 1-(3,5-bis(trifluoromethyl)phenyl)ethan-1-one of the formula:

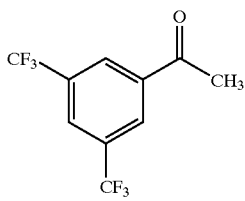

In the present invention it is preferred that the Grignard reagent is added to the acetic anhydride.

In a more preferred embodiment, following step (b) excess acetic anhydride is removed by the addition of an aqeueous solution of a base, such as sodium hydroxide, sodium bicarbonate, sodium carbonate, potassium hydroxide, and the like.

Preferred solvents for conducting the instant process comprise an organic solvent which is selected from toluene, tetrahydrofuran (G), diethyl ether, diglyme, and methyl t-butyl ether. The most preferred organic solvent is tetrahydrofuran. In the formation of the Grignard reagent, tetrahydrofuran or diethyl ether are the more preferred organic solvents and tetrahydrofuran is the most preferred organic solvent.

The $C_{1-8}$ alkyl magnesium halide is preferably selected from ethyl magnesium bromide, isopropyl magnesium chloride, ethyl magnesium chloride and isopropyl magnesium bromide, more preferably selected from ethyl magnesium bromide and isopropyl magnesium chloride, and even more preferably ethyl magnesium bromide. The magnesium employed to prepare the alkyl Grignard reagent may be in the form of magnesium granules, magnseium turnings, magnesium dust, magnesium powder, suspension of magnesium in oil, and the like. To mimimize safety risks, the use of magnesium granules is preferred.

Formation of the Grignard of 1-(3,5-bis(trifluoromethyl) phenyl)-bromide may be performed in tetrahydrofuran at between about 30 and 35° C. The reaction is exothermic and the reaction may be controlled by the rate of addition of the bromide to the magnesium slurry. The reaction mixture may be aged at reflux until <1 mol % of bromide remains. Grignard formation is usually complete within 2 hours, however reaction times of up to 5 hours give comparable yields of 1-(3,5-bis(trifluoromethyl)phenyl)ethan-1-one.

Alternatively, to minimize solvent loss, the Grignard formation may be performed in tetrahydrofuran at a temperature range between about 0 and 20° C., and preferably a reaction temperature range between about 0 and 10° C.

In the present invention, it is preferred that the Grignard reagent be added to the acetic anhydride. In the present invention, it is also preferred that an excess of acetic anhydride be present when reacting the Grignard reagent. In the present invention, it is more preferred that the Grignard reagent be added to an excess of acetic anhydride.

Surprisingly, the presence of an excess of acetic anhydride (i.e. greater than a 1:1 molar ratio) is important to providing high yields of the desired product. When the acetic anhydride was added to the Grignard reagent at 20° C. an exothermic reaction resulted which produced a bis-adduct of the formula:

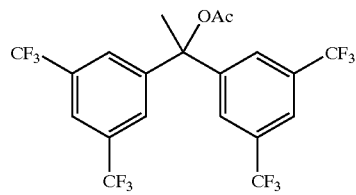

Surprisingly, however, when the Grignard reagent was added to acetic anhydride, little byproduct was formed and 1-(3,5-bis(trifluoromethyl)phenyl)ethan-1-one was obtained in 85–90% yield.

In the present invention, it is preferred that the Grignard reagent is added to cooled acetic anhydride. In the present invention, it is more preferred that the Grignard reagent is added slowly (over a period of 1–2 hr, for example) to a cooled mixture of acetic anhydride in either tetrahydrofuran or tert-butyl methylether, maintaining the temperature at below about 5° C., or alternatively between about −10 to −15° C.

In the addition of the Grignard reagent with acetic anhydride, it is preferred that the temperature of the acetic anhydride upon addition of the Grignard reagent be less than about 5° C., more preferrably, less than about −10° C., it is even more preferrably less than about −15° C. Upon addition of the Grignard reagent, the temperature of the reaction mixture may be raised to about 5° C.

In a preferred additional embodiment, isolation of 1-(3,5-bis(trifluoromethyl)phenyl)ethan-1-one may be achieved by adding cold water to the reaction mixture followed by the slow addition of aqueous solution of a base to hydrolyze the excess acetic anhydride. The base may be an inorganic base selected from sodium hydroxide, potassium hydroxide, sodium bicarbonate, potassium carbonate, and the like. A preferred base is sodium hydroxide. The pH of the aqueous layer is preferably brought to greater than 10. When the pH is greater than 10, the mixture is extracted with tert-butyl methylether. The extracts are washed with aqueous sodium bicarbonate and aqueous sodium chloride and the solvents are removed by distillation.

The 1-(3,5-bis(trifluoromethyl)phenyl)ethan-1-one obtained in accordance with the present invention may be used as starting material in further reactions directly or following distillation. The isolated product can be distilled at atmospheric or reduced pressure to provide a clear colorless oil with BP=185–189° C.

Many of the starting materials are either commercially available or known in the literature and others can be prepared following literature methods described for analogous compounds. The skills required in carrying out the reaction and purification of the resulting reaction products are known to those in the art. Purification procedures include crystallization, distillation, normal phase or reverse phase chromatography.

The following examples are provided for the purpose of further illustration only and are not intended to be limitations on the disclosed invention.

EXAMPLE 1
3,5-Bis(Trifluoromethyl)Bromobenzene

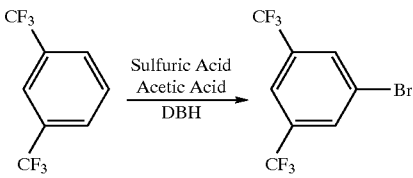

| Materials | MW | Density | Amount | Mmol | Equiv. |
|---|---|---|---|---|---|
| 1,3-Bis(trifluoromethyl)benzene | 214.1 | 1.38 | 107 g | 500 | 1.0 |
| 96% H$_2$SO$_4$ | | | 142 mL | | |
| Glacial HOAc | | | 22 mL | | |
| 1,3-Dibromo-5,5-dimethylhydantoin | 285.93 | | 77.25 g | 270 | 1.08 (Br$^+$) |
| 5N Aq NaOH | | | 75 mL | | |

To glacial acetic acid (22.0 mL), cooled to 15° C. in a 1 L 3-n RB flask (equipped with mechanical stirrer, thermocouple, and addition funnel), was added concentrated (96%) sulfuric acid (142 mL) in one portion. An exothermic heat of solution raised the temperature to 35° C. After cooling to 25° C., 1,3-bis(trifluoromethyl)benzene (107 g, 500 mmol) was added. With the acid mixture rapidly stirring, 1,3-dibromo-5,5-dimethylhydantoin (77.25 g; 270 mmol) was added over 2 min to give a multiple phase mixture (solid and two liquid). An exothermic reaction occured that raised the internal temperature to ~40° C. (jacket cooling at 15° C.). After the reaction temperature began to drop (after 5 min) the reaction mixture was maintained at 45° C. for 4.5 hr.

The rate and selectivity of the bromination is highly dependent on the agitation of the two phase reaction. Slower stirring increases the amount of bis-bromination and slows the overall rate of reaction. The reaction mixture remains heterogeneous throughout the reaction and the organic phase separates when agitation is interrupted. At the end of the reaction, the phases separate slowly (bromide density= 1.699). The rate of bromination is also dependent on the ratio of acetic to sulfuric acid. Progress of the reaction is monitored by GC analysis, as follows.

Sample: ~50 µl of mixed phase, dilute with cyclohexane (1.5 mL), wash with water (1 mL), then 2N NaOH (1 mL), separate and inject.

Resteck RTX-1701 [60 meter×0.320 mm]: 100° C.; ramp: 5° C./min to 200° C.; 200° C. for 10 min; Flow 1.15 mL/min R$_t$:1,3-bis(trifluoromethyl)benzene: 7.0 min
3,5-bis(trifluoromethyl)bromobenzene: 9.4 min
Biaryl: 19.2 min The mixture was cooled to 2° C. and poured slowly into cold water (250 mL). The mixture was stirred vigorously for 10 min, allowed to settle, and the lower organic layer was separated and washed with 5N NaOH (75 mL) to give 145.1 g of a clear, colorless organic layer.

The assay yield of 1,3-bis(trifluoromethyl)bromobenzene was 93.7% (137.3 g, 469 mmol), which contained 0.6% 1,3-bis(trifluoromethyl)benzene, 1.0% 1,2-dibromo-3,5-bis(trifluoromethyl)benzene, and 0.3% 1,4-dibromo-3,5-bis-(trifluoromethyl)benzene. Total isomer byproducts measured by GC were 2.0 mol %.

EXAMPLE 2
1-(3,5-Bis(Trifluoromethyl)Phenyl)Ethan-1-One

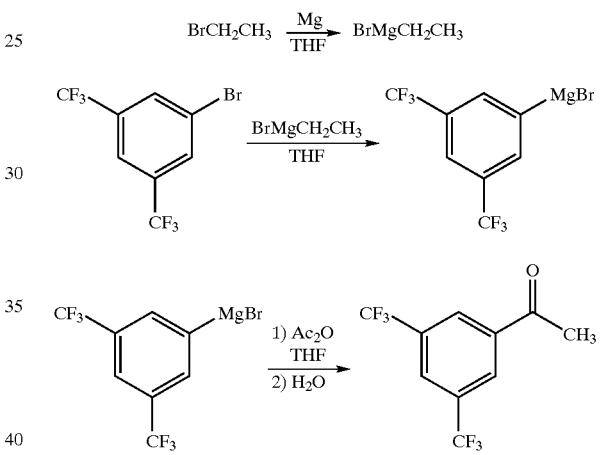

| Materials | MW | Density | Amount | Equiv |
|---|---|---|---|---|
| 3,5-Bis(trifluoromethyl)bromobenzene | 293.03 | 1.699 g/L | 80 kg | 1.0 |
| Magnesium granules, 20 mesh | 24.3 | | 7.33 kg | 2.1 |
| Acetic Anhydride | 102.1 | 1.08 g/L | 97.6 kg | 4.5 |
| THF (KF = 60 µg/mL) | | | 560 kg | |
| MTBE | | | 120 kg | |
| Water | | | 100 kg | |
| 5N NaOH | | | 98.9 kg | |
| 5% NaHCO3 (aq.) | | | 80 kg | |

Step A: Preparation of Seeds of Ethyl Magnesium Bromide

To a 20 L reactor equipped with stirring apparatus and under N$_2$ was added magnesium granules (0.33 kg), THF and a small amount of iodine flakes. A small amount of ethylbromide was added dropwise followed by THF (9.37 kg). To the stirred reaction mixture was added dropwise a solution of ethylbromide (1.56 kg) in THF (2.34 kg) such that the reaction temperature was maintained below 35° C. Upon completion of addition, the reaction mixture was stirred at 30–35° C. for 1 hour.

Step B: Preparation of 1-(3,5-Bis(Trifluoromethyl)Phenyl) Magnesium Bromide by Grignard Exchange Reaction To a 500 L reactor equipped with stirring apparatus and under N$_2$ was added magnesium granules (7.0 kg) and THF (200 kg) and the suspension of ethyl magnesium bromide in THF from Step A. To the stirred reaction mixture was added dropwise a solution of ethylbromide (32.7 kg) in THF (49.1 kg) such that the reaction temperature was maintained below 35° C. Upon completion of addition, the reaction mixture was stirred at 30–35° C. for 1 hour. A portion of the suspension of ethyl magnesium bromide in THF was reserved as seeds for later batches.

To the stirred reaction mixture was added dropwise a solution of 3,5-bis(trifluoromethyl)bromobenzene (120 kg) in THF (120 kg) such that the reaction temperature was maintained below 30° C. The reaction mixture was held below 30° C. until conversion was more than 95%. The reaction was monitored by HPLC (sample preparation: 100 µL sample quenched into 3.5 mL of 1:1 THF:2N HCl, then diluted to 100 mL in 65:35 acetonitrile:pH 6 buffer).

Step C: Coupling Reaction

To a solution of acetic anhydride (97.6 kg) in TBF (207.9 kg) in a 1500 L reactor was added dropwise with stirring the solution of 1-(3,5-bis(trifluoromethyl)phenyl)magnesium bromide from Step B such that the reaction temperature was maintained below 5° C. and then the reaction mixture was kept at below 5° C. for 0.5 hour.

Step D: Hydrolysis

To the reaction mixture from Step C water (195.1 kg) was added dropwise such that the reaction temperature was maintained below 5° C. The reaction mixture was heated at 55–65° C. for 0.5 hour with stirring, then cooled to below 15° C. and the phases were allowed to separate. Methyl tert-butyl ether (120 kg) was added and the mixture was neutralized by the addition with stirring of 5N NaOH (98.9 kg) [25% NaOH (67.3 kg, 0.44 eq/acetic anhydride) and water (31.6 kg)] was added dropwise over 1 hr, until a pH of greater than 10. The organic phase was separated and washed with 5% NaHCO$_3$ (80 kg) [NaHCO$_3$ (90.75 kg) and water (76 kg)]. The organic phase was separated and concentrated at a temperature below 95° C. The concentrate was then distilled at reduced pressure at a temperature below 125° C. to give 1-(3,5-bis(trifluoromethyl)phenyl)ethan-1-one.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of the formula:

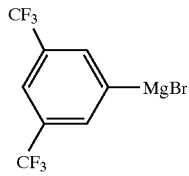

which comprises:
treating 3,5-bis(trifluoromethyl)bromobenzene of the formula:

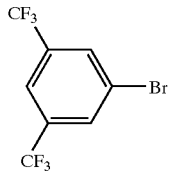

with ethyl magnesium bromide or isopropyl magnesium chloride in an organic solvent to give the compound of the formula:

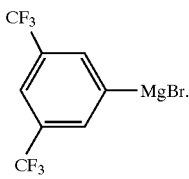

2. A process for the preparation of a compound of the formula:

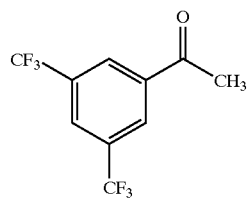

which comprises:
a) treating 3,5-bis(trifluoromethyl)benzene of the formula:

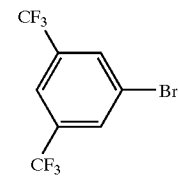

with a Grignard reagent selected from:
ethyl magnesium bromide, isopropyl magnesium chloride, ethyl magnesium chloride and isopropyl magnesium bromide;
in an organic solvent to form 1-(3,5-bis(trifluoromethyl) phenyl)magnesium bromide of the formula:

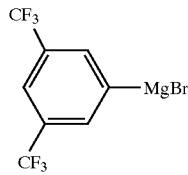

b) followed by contacting the 1-(3,5-bis(trifluoromethyl)-phenyl)magnesium bromide with acetic anhydride in an organic solvent to give the compound of the formula:

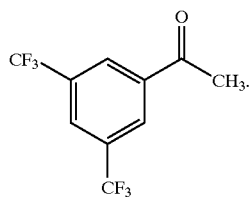

3. A process for the preparation of a compound of the formula:

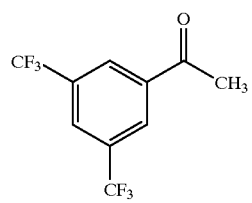

which comprises:

a) treating 3,5-bis(trifluoromethyl)benzene of the formula:

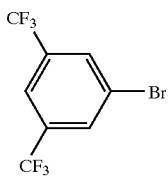

with a Grignard reagent selected from: ethyl magnesium bromide and isopropyl magnesium chloride;
in an organic solvent to form 1-(3,5-bis(trifluoro-methyl)phenyl)magnesium bromide of the formula:

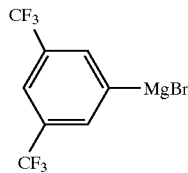

b) followed by contacting the 1-(3,5-bis(trifluoromethyl)phenyl)-magnesium bromide with acetic anhydride in an organic solvent to give the compound of the formula:

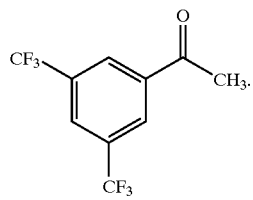

4. The process of claim 1 wherein the organic solvent comprises a solvent which is selected from: tetrahydrofuran, toluene, diethyl ether, diglyme, and methyl t-butyl ether.

5. The process of claim 1 wherein the organic solvent comprises tetrahydrofuran.

6. The process of claim 2 wherein the organic solvent comprises a solvent which is selected from: tetrahydrofuran, toluene, diethyl ether, diglyme, and methyl t-butyl ether.

7. The process of claim 2 wherein the organic solvent comprises tetrahydrofuran.

8. The process of claim 3 wherein the organic solvent comprises a solvent which is selected from: tetrahydrofuran, toluene, diethyl ether, diglyme, and methyl t-butyl ether.

9. The process of claim 3 wherein the organic solvent comprises tetrahydrofuran.

10. The process of claim 2 wherein the formation of the 1-(3,5-bis(trifluoromethyl)phenyl)magnesium bromide is conducted at a temperature range below about 30° C.

11. The process of claim 3 wherein the formation of the 1-(3,5-bis(trifluoromethyl)phenyl)magnesium bromide is conducted at a temperature range below about 30° C.

12. The process of claim 2 wherein the 1-(3,5-bis(trifluoro-methyl)phenyl)magnesium bromide is added to acetic anhydride.

13. The process of claim 3 wherein the 1-(3,5-bis(trifluoro-methyl)phenyl)magnesium bromide is added to acetic anhydride.

14. The process of claim 2 wherein the 1-(3,5-bis(trifluoro-methyl)phenyl)magnesium bromide is added to an excess of acetic anhydride.

15. The process of claim 3 wherein the 1-(3,5-bis(trifluoro-methyl)phenyl)magnesium bromide is added to an excess of acetic anhydride.

16. The process of claim 2 wherein the temperature of the acetic anhydride upon addition of the 1-(3,5-bis(trifluoromethyl)phenyl)magnesium bromide is less than about 5° C.

17. The process of claim 3 wherein the temperature of the acetic anhydride upon addition of the 1-(3,5-bis(trifluoromethyl)phenyl)magnesium bromide is less than about 5° C.

18. The process of claim 2 wherein following step (b), excess acetic anhydride is removed by the addition of an aqeueous solution of a base.

19. The process of claim 3 wherein following step (b), excess acetic anhydride is removed by the addition of an aqeueous solution of sodium hydroxide.

20. A process for the preparation of 1-(3,5-bis (trifluoromethyl)-phenyl)ethan-1-one which comprises the reaction of 3,5-bis(trifluoromethyl)-bromobenzene with ethyl magnesium bromide in tetrahydrofuran to form 1-(3,5-bis(trifluoromethyl)phenyl)magnesium bromide followed by addition of the Grignard reagent to an excess of acetic anhydride to give 1-(3,5-bis(trifluoromethyl)-phenyl)ethan-1-one.

\* \* \* \* \*